United States Patent [19]

Wright

[11] 4,236,889
[45] Dec. 2, 1980

[54] DENTAL CLEANING DEVICE

[76] Inventor: Winston F. Wright, 2660 Fair Cir., Reno, Nev. 89503

[21] Appl. No.: 39,831

[22] Filed: May 17, 1979

[30] Foreign Application Priority Data

Mar. 28, 1978 [GB] United Kingdom ............... 12007/78

[51] Int. Cl.³ ............................................. A61C 17/00
[52] U.S. Cl. .................................. 433/86; 128/62 A; 433/88
[58] Field of Search ............................ 433/86, 88, 89; 128/62 A, 66, 229, 230

[56] References Cited

U.S. PATENT DOCUMENTS

| 3,195,537 | 7/1965 | Blasi | 128/62 A X |
| 3,405,710 | 10/1968 | Kovach | 128/62 A X |
| 3,535,726 | 10/1970 | Sawyer | 128/62 A X |
| 3,703,170 | 11/1972 | Ryckman, Jr. | 128/62 A X |
| 3,993,054 | 11/1976 | Newman | 128/230 X |

Primary Examiner—William A. Cuchlinski, Jr.
Attorney, Agent, or Firm—Charles E. Temko

[57] ABSTRACT

A portable dental cleaning device includes a housing having two separate chambers divided by a partition. A motor driven pump disposed in one chamber receives a cleaning slurry from the other chamber and discharges it under vibration pressure through a nozzle disposed outwardly of the housing for cleaning teeth and massaging gums. A switch mounted on the housing permits manual flow control of the cleaning slurry through the device.

8 Claims, 2 Drawing Figures

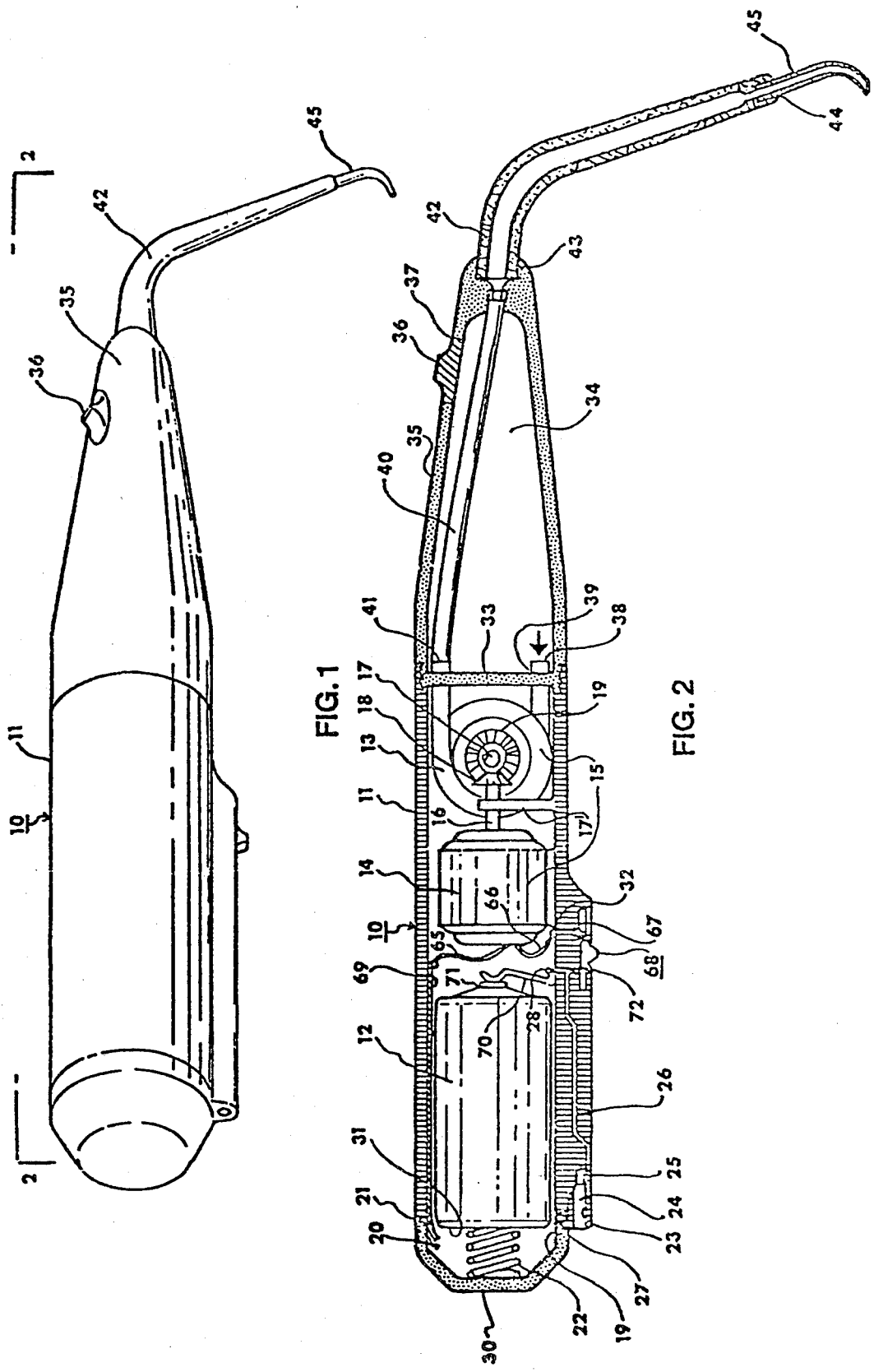

DENTAL CLEANING DEVICE

This invention relates to an improved device for cleaning teeth and massaging gums with a cleaning abrasive slurry substance which is discharged from such device under pressure through a nozzle into the oral cavity. More particularly, the present invention relates to a portable dental cleaning device for treatment of teeth and gums by use of a slurry jet dispensed at a controlled velocity and directed into the oral area to be cleansed.

It is well known to apply a liquid stream to teeth and gums using an apparatus which includes pumping means lodged in a housing and a separate open-top reservoir containing a cleaning liquid which is transferred by pumping means into a tubing and discharged through a nozzle connected thereto. This type of a cleaning device is cumbersome, heavy and inconvenient in transportation from one place to another, especially in travels.

It is, therefore, the primary object of this invention to provide an improved dental cleaning device adapted for efficient cleaning of the oral cavity.

Another object of the invention is the provision of a self-contained portable device for cleaning teeth and massaging gums with a slurry discharged therefrom under pressure and at a high velocity.

A still further object of the invention is to provide a hand-held device for oral hygiene, such device being small, light and compact and convenient in travelling as it can easily be placed in a cosmetic case or a utility kit.

The foregoing and other objects of this invention will become apparent from the following description considered in conjunction with the accompanying drawing, in which:

FIG. 1 is a perspective view of the device of this invention;

FIG. 2 is a vertical sectional view taken along line 2—2 in FIG. 1.

In accordance with this invention, there is provided a portable, self-contained, unitary, hand-held dental cleaning device which comprises, in combination, an elongated, hollow housing comprising a first chamber containing a pump connected to an electrical motor and means for supplying energy to the motor and a second chamber which is adapted to contain a slurry. A vertical partition separates the two chambers thus providing space in the first chamber for the pump, the motor and the means for supplying energy therefor, while the independent second chamber is adapted for holding a supply of the cleaning slurry substance. The partition includes two apertures for a pump inlet conduit which connects the pump with the second chamber and for a pump outlet conduit which connects the pump to one end of an elongated tube disposed in the second chamber. The opposite end of the elongated tube is, in turn, connected to a discharge nozzle which extends outwardly from the second chamber. The two conduits which pass through the two apertures are in a sealing engagement with the partition to prevent leakage of the slurry from the second chamber into the first chamber. The second chamber is provided with an opening in its upper wall for feeding a dental cleaning slurry and a cap which closes tightly the opening. A switch means is provided for control of the speed of rotation of the motor thereby regulating the flow rate of the cleaning slurry when discharged from the device.

In the preferred embodiment of the invention, as illustrated in FIG. 1 and FIG. 2, the dental cleaning device 10 of this invention is of a generally cylindrical configuration and is comprised of a one piece housing containing two chambers. The first chamber 11 is adapted to contain a battery 12, an electrical motor 14 and pump 15 preferably of the centrifugal type actuatable by motor 14. The motor 14 is affixed by conventional mounts 32 to the inner wall of first chamber 11 and is connected to pump 15 by a rotatable shaft 16 which traverses an opening in vertical riser 17' and the free end of which is provided with pinion gear 18 meshing with teeth of beveled gear 19 mounted on drive shaft 17 of pump 15.

The rear end portion 20 of dental device 10 comprises a threaded closure cap 30 which engages the threaded portion 21 of device 10. The inner surface of cap 30 formed of a conductive metal is in contact with a coil spring 22 which is situated between the inner portion of cap 30 and the bottom pole 31 of battery 12 and thus electrically connects the bottom pole 31 with the inner surface of the cap 30.

The dental device 10 is provided with a conventional charging unit receptacle 23 which comprises a pair of concentric holes 24 and 25 insulatedly separated from each other and provided with a pair of leads 26 and 27. Lead 26 is connected to switch contact 28 and lead 27 is connected to the threaded portion 29 which is in contact with the threads and the metallic inner surface of cap 30.

The first chamber 11 is separated from the adjacent second chamber 34 by a water-tight vertical partition 33 which includes two apertures through which pass an inlet conduit 38 and a discharge conduit 13, respectively, each conduit being in sealing engagement with partition 33 to prevent the cleaning slurry introduced in the chamber 34 from leaking into first chamber 11. An opening 37 is provided in the portion of the upper wall of second chamber 34 for introduction of the slurry or any desired antiseptic slurry mixture which may contain a finely ground abrasive compound. A closure cap 36, preferably of the screwing type, is provided to prevent spilling or leakage of the slurry from chamber 34.

The inlet conduit 38 of pump 15 is tightly fitted into aperture 39 in the partition 33 and its open end extends somewhat into the second chamber 34, while an elongated tube 40 is connected at one end to outlet 41 of discharge conduit 13 which likewise projects through the other aperture in partition 33. The opposite end of tube 40 is connected at its end portion 43 to a removably engaged nozzle 42 which extends outwardly from chamber 34. The nozzle 42 terminates at its outer end in a curved tip 45 having a passageway with an outlet opening, the opposite end of tip 45 being releasably in a water-tight engagement with corresponding opening 44 in nozzle 42.

Motor 14 is provided with a pair of insulated electrical wires 65 and 66, the former being connected to a metallic strip 69 which extends between the battery 12 and the inner wall of first chamber 11 up to the thread at the rear end portion 20 of device 10 with which it makes contact. The latter wire 66 is connected to contact terminal point 67 of a variable speed switch means 68 mounted on the outside wall of first chamber 11.

A substantially vertically extending conductive support member 70 affixed at one end to switch contact 28 contacts the front pole 71 of battery 12. In this manner, the electrical circuitry to motor 14 is completed. A sliding bar 72 which is accessible externally of the housing for actuating switch 68 is mounted adjacent thereto and connected therewith in a conventional manner.

In operation, the closure screw cap 36 is removed and a desired volume of a cleaning slurry, preferably a limpid slurry suspension of a finely ground, soft abrasive material, such as limestone, is fed through opening 37 into second chamber 34 and the opening 37 is closed by screw cap 36. The motor 14 is energised by closing the variable speed switch 68 which provides control of the rate of flow of the cleaning slurry through pump 15 coacting with the motor and its discharge through nozzle 42. It will be understood by persons skilled in this art that the action of the centrifugal pump which is actuated by the motor causes the slurry to be urged therethrough in a pressurised flow and be discharged through tube 40 and nozzle 42 into the location in the mouth to be treated. The manually controllable switch 68 permits a control of speed of rotation of the motor and thus a control of movement and of vibration of the abrasive slurry mixture through the pump at varying flow rates reaching sonic or supersonic vibration speed at the highest speed of rotation of the motor thereby producing a rapid and highly efficient cleaning action of teeth and gum area.

While it is preferred to operate the cleaning device of this invention with a rechargeable battery as a sole means for supply of energy to the motor, it is within the scope of the invention to use outside current by simply providing a conventional electrical conduit to be plugged into a standard electric outlet thereby providing an alternative power source for the cleaning device.

It will be apparent from the foregoing description that the device of this invention provides a convenient means for cleaning oral cavity through the action of a controllable jet stream of a cleaning slurry which effectively cleanses teeth and massages the gum area. Such action is achieved using a small, hand-held, self-contained unit which may be carried easily from one place to another and which is particularly convenient to pack in a small travelling suitcase. Furthermore, the device of this invention, while of a simple construction, is capable to emit a powerful jet or alternating jet of a cleaning slurry substance at a sonic vibration speed thereby producing a superior effect in providing oral hygiene.

Although this invention has been described in its preferred embodiment, various modifications may be made in the disclosed device without departing from the scope of the invention in its broadest aspects.

I claim:

1. A self-contained, portable dental cleaning device comprising an elongated housing which comprises a first chamber containing a pump connected to an electrical motor and means for supplying energy to said motor, a switch means mounted on said device for manual control of the speed of rotation of said motor, a second chamber being adapted to contain a slurry substance, a vertical partition separating said first chamber from said second chamber, said partition including two apertures, an inlet conduit connecting said second chamber with said pump and an outlet conduit connecting said pump to one end of an elongated tube disposed in said second chamber, the opposite end of said tube being connected to a discharge nozzle extending outwardly from said second chamber, each of said conduits being in a sealing engagement with said partition, said second chamber having an opening for introduction of a dental cleaning slurry and a cap for tightly closing said opening.

2. The dental cleaning device as claimed in claim 1 wherein said pump is centrifugal and is actuatable by gear means connected with said motor.

3. The dental cleaning device as claimed in claim 1 wherein said means for supplying energy to said motor is a battery situated in said first chamber.

4. The dental cleaning device as claimed in claim 1 wherein said inlet conduit is adapted to receive said dental cleaning slurry introduced into said second chamber for passage through said pump.

5. The dental cleaning device as claimed in claim 1 wherein said dental cleaning slurry is conducted by said pump into said outlet conduit to be discharged under pressure through said nozzle upon actuation of said pump.

6. The dental cleaning device as claimed in claim 5 wherein said device is capable of discharging said dental cleaning slurry which comprises a suspension of a finely ground abrasive material at a sonic vibration speed.

7. The dental cleaning device as claimed in claim 1 wherein said nozzle is removably connected to the end of said elongated tube within said second chamber.

8. The dental cleaning device as claimed in claim 1 wherein said switch means is mounted on the outside wall of said first chamber.

* * * * *